United States Patent [19]

McIntyre et al.

[11] Patent Number: 4,646,781

[45] Date of Patent: Mar. 3, 1987

[54] DIAPHRAGM VALVE FOR MEDICATION INFUSION PUMP

[75] Inventors: John McIntyre, Foster City; Lanny A. Gorton, Sunland, both of Calif.

[73] Assignee: Pacesetter Infusion, Ltd., Sylmar, Calif.

[21] Appl. No.: 873,439

[22] Filed: Jun. 5, 1986

Related U.S. Application Data

[63] Continuation of Ser. No. 731,307, May 7, 1985, abandoned.

[51] Int. Cl.$^4$ ............................................. F16K 15/14
[52] U.S. Cl. ............................... 137/512.4; 137/859; 251/368; 417/560; 417/566
[58] Field of Search ............... 137/496, 512.4, 859; 417/560, 566; 604/327

[56] References Cited

U.S. PATENT DOCUMENTS

| | | | |
|---|---|---|---|
| 2,376,712 | 5/1945 | Moran | 137/859 X |
| 2,758,609 | 8/1956 | Dickert | 137/859 |
| 2,980,032 | 4/1961 | Schneider | 417/479 |
| 3,401,719 | 9/1968 | Rosser | 137/859 X |
| 3,886,937 | 6/1975 | Bobo | |
| 4,153,186 | 5/1979 | Nye | 137/859 X |
| 4,181,477 | 1/1980 | Litt | 417/560 |
| 4,244,378 | 1/1981 | Brignola | 137/843 X |
| 4,265,601 | 5/1981 | Mandroian | 417/379 |
| 4,310,017 | 1/1982 | Raines | 137/533 |
| 4,411,603 | 10/1983 | Kell | 417/479 |
| 4,468,221 | 8/1984 | Mayfield | 604/152 |

FOREIGN PATENT DOCUMENTS

| | | | |
|---|---|---|---|
| 690897 | 4/1953 | United Kingdom | 137/496 |
| 751289 | 6/1956 | United Kingdom | 137/859 |
| 1475683 | 6/1977 | United Kingdom | 137/859 |

Primary Examiner—Robert G. Nilson
Attorney, Agent, or Firm—L. Lee Humphries; Leslie S. Miller

[57] ABSTRACT

A valve, suitable for use in small medical devices and which can readily be made of medical grade materials, comprises an elastic diaphragm stretched over a protruding surface, preferably of spherical or convex shape. The diaphragm has a ring of holes concentrically around a hole in the protruding surface. A mating recess, connected to a conduit, fits over the protruding surface. The elastic material is held in place at or near the opening of the recess. The holding structure may also serve to seal the valve. A dual arrangement provides an input and an output valve in combination.

21 Claims, 12 Drawing Figures

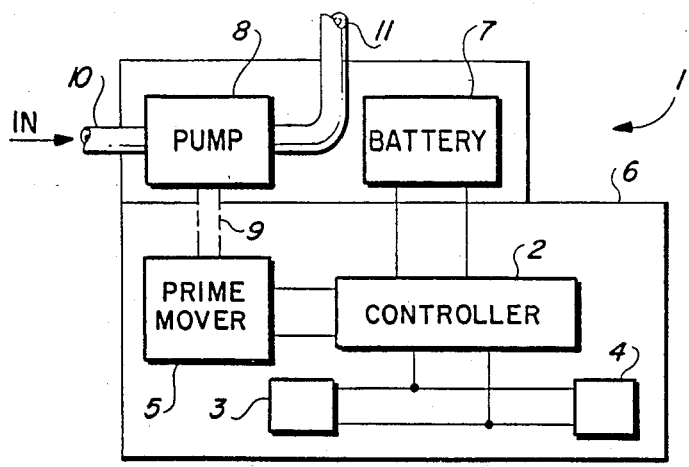
FIG.1
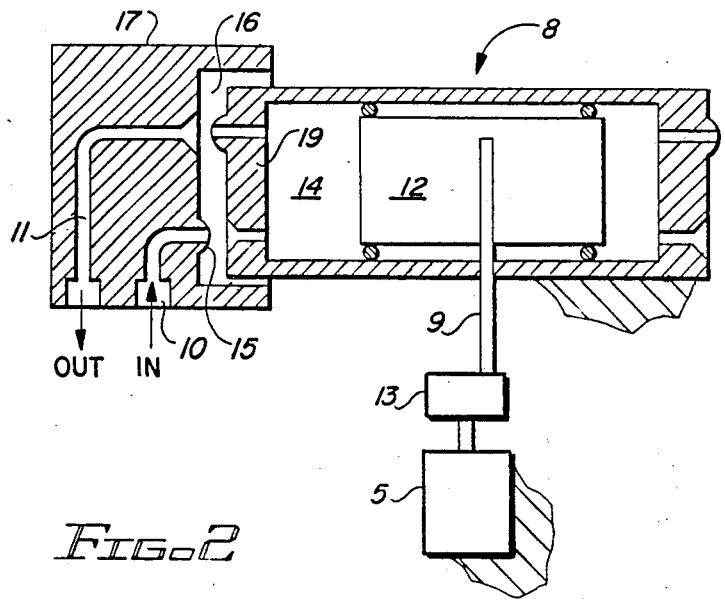
FIG.2
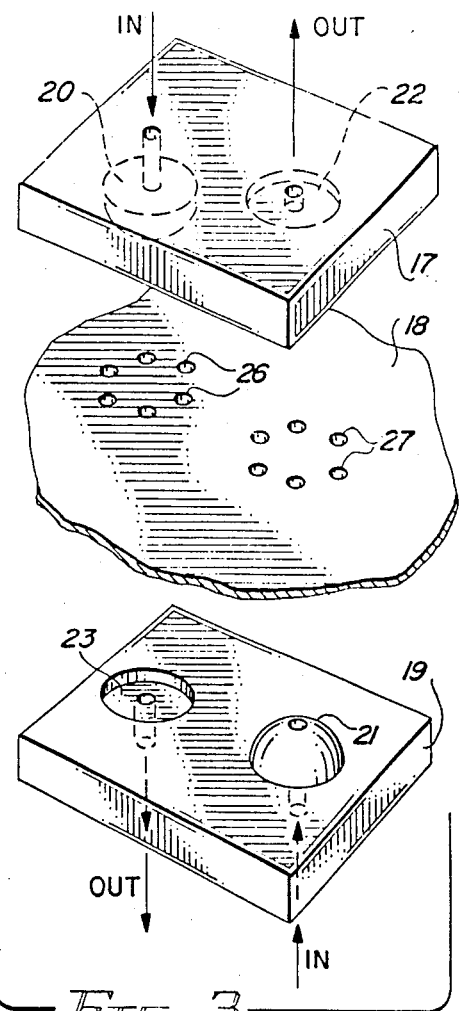
FIG.3
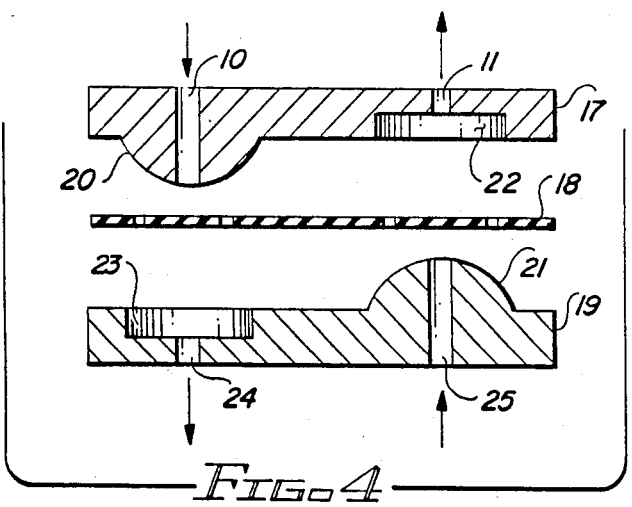
FIG.4
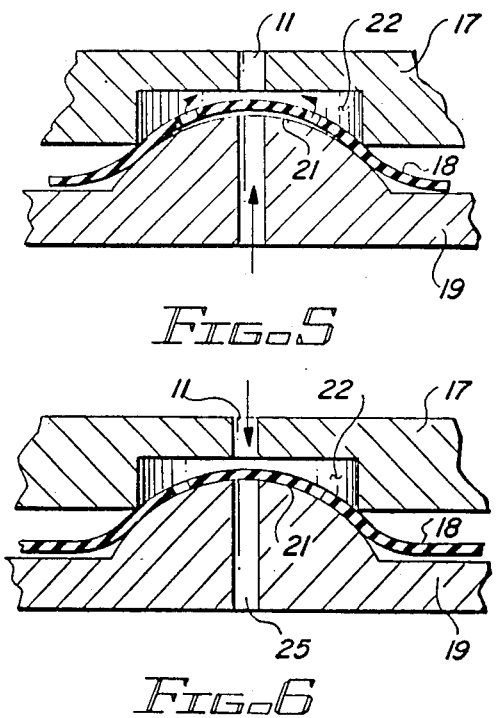
FIG.5
FIG.6

DIAPHRAGM VALVE FOR MEDICATION INFUSION PUMP

This is a continuation of co-pending application Ser. No. 731,307, filed on May 7, 1985, now abandoned.

BACKGROUND OF THE INVENTION

This invention relates to an improved valve particularly suited for application in small medical devices, particularly in infusion pumps, which are used to inject fluids into a patient. Such a valve is easily manufactured and operates reliably over a long period of life.

In medical devices, only medical grade materials may be used because of the contact with the medicine or other fluids which are administered. The device of the invention is readily manufactured of such materials and, also, does not introduce or foster contamination.

Infusion pumps, sometimes referred to as i.v. pumps, are utilized to pump fluids intravenously (and occasionally, intra-arterially,) into a patient. Some of the most common uses of such devices are to inject electrolytes, antibiotics, insulin and plasma into a patient. Other fluids, including but not limited to other drugs, may also be injected by such devices.

The valve of the invention may be made very small and yet operate effectively as required in the control of fluid flow. It is a unidirectional, passive valve; that is, it opens or closes under pressure (or flow) in the conduit in which it is disposed and permits flow in one direction only. It provides a positive seal against flow in the backward direction and yet opens readily for flow in the forward direction. Further, it may be constructed so as not to restrict forward flow significantly, and allow only a small pressure drop. In prior valves, constructed of rubber, silicone rubber or the like, the material would tend to wrinkle, elongate and creep into voids, causing several problems. The valve of this invention is substantially superior in that such undesirable results are minimized.

The valve will operate under a low pressure and in small channels.

It is, therefore, an object of this invention to provide a valve that may be easily manufactured in small sizes.

It is another object of this invention to provide a valve that may be manufactured entirely of medical grade materials.

Another object of this invention is to provide a valve that is reliable and operates effectively over a long period of time.

Still another object of this invention is to provide a valve which is suitable for use in a medical device.

Further objects and features will become apparent to those skilled in the art, from the description set forth below.

DESCRIPTION OF THE DRAWINGS

FIG. 1 illustrates an infusion system which may utilize the valve of the invention.

FIG. 2 is a cross-section of a double-acting pump showing how the valve may be used both for output and intake.

FIG. 3 is an exploded view of the parts of two valves disposed in opposite directions.

FIG. 4 is a cross-section of two valves disposed in opposite directions.

FIG. 5 is a cross-section which shows the flow of fluid through the valve.

FIG. 6 is a cross-section which shows the valve sealing against the backward flow of fluid.

DETAILED DESCRIPTION OF THE PREFERRED EMBODIMENT

Figure 7:
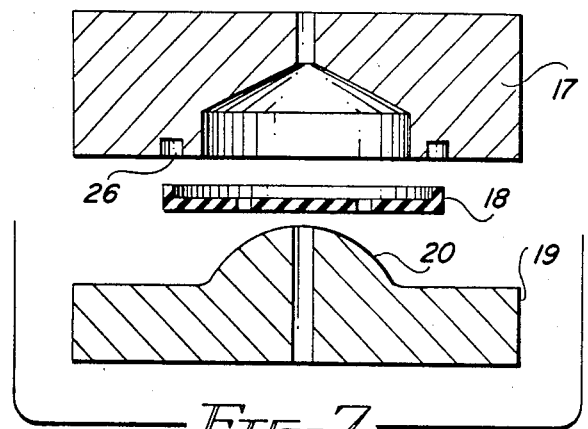
FIG. 7 illustrates an embodiment in which the diaphragm is self-adjusting as the valve is assembled.

FIG. 1 illustrates an infusion system 1, which in this case might be, for example, an insulin infusion pump, having a controller 2 and various other microelectronic components 3 and 4. Prime mover 5 is contained within the body 6 of the infusion system 1 and receives power from battery 7, to drive pump 8. The prime mover 5 may be, for example, a rotating motor, step motor or a solenoid. In addition, prime mover 5 may be a hydraulic motor. Dotted lines 9 are intended to portray the different possibilities of driving the pump 8, whether it be by direct drive or fluid or otherwise. The term "prime mover", or "driver" is intended to cover all suitable devices. If the drive system is hydraulic, the valve of the invention may be used in the drive system, if desired, although it is most suitable for flow control in or in association with, the pump 8. In FIG. 1 fluid enters the pump through intake conduit 10 and exits through output conduit 11.

In FIG. 2 is shown a cross-section of a double-acting cylindrical pump 8 in which piston 12 moves within a cylinder 14, driven by drive means 9 connected to eccentric 13 and rotating motor 5. When piston 12 moves to the right, on the intake stroke, fluid is drawn in through intake conduit 10 and its associated intake valve 15. When piston 12 moves to the left, on the pump stroke, the fluid is pumped from the cylinder 12 through the output valve 16 and the output conduit 11. On the intake stroke, output valve 16 shuts tightly and on the output stroke, intake valve 15 shuts tightly. A diaphragm such as diaphragm 18 in FIG. 3 would be required to be disposed between body elements 17 and 19 so as to be a part of valves 15 and 16.

FIG. 3 is an exploded view of the essentials of the valve. Two body elements 17 and 19 hold a flexible diaphragm 18 tightly between them. The elements may be made of any rigid plastic, or even hard rubber, so long as the material used is biologically compatible and suitable for medical use. The plastics include the acrylics, polysulfins, polyethylenes, polycarbonates and others. The diaphragm may be made of any medical grade silicone rubber, natural rubber or other suitable flexible, elastic, or resilient, material. The thickness of the diaphragm may be on the order of from 3 to 10 mils for conduits which are 1/16" to ⅛" in diameter. Other size conduits and thickness of valves may, of course, be utilized. Pressure on said valve, as an input valve or an output valve, may be on the order of from −4 to +20 psi. Of course, the "break" pressure, the pressure at which the valve opens, varies with the thickness of the diaphragm material, its elasticity, and the tension placed upon it. In FIG. 3 two valves are shown, one for each direction of flow. Each of the elements 17 and 19 has a raised or protruding portion, 20 and 21, respectively, which may be a portion of a sphere, frusto-conical, convex or other protruding surface. Mating with such raised portions 20 and 21 are corresponding recesses 23 and 22, respectively, which form chambers in the portion of the opposing element opposite the raised portions 20 and 21. Such recesses 22 and 23 may be constructed generally to fit the protruding surfaces 21 and 20, respectively, but preferably are right circular cylinders if the protruding surfaces 20 and 21 are spherical in shape. Thus, it is evident that the protruding surfaces 20 and 21 and the recesses 22 and 23 need not necessarily be curved. The recesses 22 and 23 are preferably not curved and the protruding surfaces 20 and 21, preferably, are curved. At any rate, the protruding surfaces 20 and 21 must fit at least partially into the recesses 23 and 22, respectively. A line of contact is sufficient, but a wider area of contact may be utilized. The line or area of contact, grips the elastic diaphragm 18 and seals the valve assembly from leakage from the fluid path to the outside. Also, suitable preloading of the diaphragm 18 can be obtained by the areas of contact between the protruding surfaces 20. and 21 and the recesses 22 and 23. Each recessed surface 22, 23 as well as each protruding surface 20, 21 has a conduit 10, 11, 24, 25 therethrough. Preferably, each conduit 10, 11, 24, 25 is disposed to emerge in the center of the surface 20, 21, 22, 23 with which it is associated. Each conduit 10, 11, 24, 25 may, however, be located to emerge at a point other than the center of the recess 22, 23 or the protruding surface 20, 21. Also, the holes 26 and 27 need not entirely encompass the conduits 10, 11, 24, 25, but may be disposed only on one side of the conduits 10, 11, 24, 25. The preferred construction, however, is as shown in FIGS. 3 and 4.

FIG. 4 is a cross-section of the dual valve arrangement, in which the valves are oppositely directed, such as one for intake and one for output. The mating between the two pump body parts 17 and 19 is illustrated. As can be seen in FIG. 4, the conduit 10 permits fluid flow out the apex of protruding surface 20 (where the elastic diaphragm 18 is flexed greatest) and through the holes 26 (FIG. 3). The fluid flows into chamber 23 and through conduit 24. Similarly, a conduit 25 emerges at the apex of protruding surface 21 and fluid flows from conduit 25 through the holes 27 (FIG. 3) in diaphragm 18 on into chamber 22 and out through conduit 11. The holes 26 and the holes 27 are shown as disposed concentrically with the conduits 10 and 25. As previously indicated, they need not be so disposed and may be eccentrically located with respect to the chambers 22, 23 and the protruding surfaces 20, 21 and the conduits 10, 11, 24, 25 need not emerge through such surfaces 20, 21, 22, 23 at a central location. However, having the conduits 10, 11, 24, 25 centrally located and the holes 26, 27 concentrically around the conduits 10, 11, 24, 25 is preferred.

FIG. 5 illustrates how element 17 fits to element 19 and how a portion of the diaphragm 18 is held between them. In the embodiment shown, there is an edge, or line, contact, inasmuch as chamber 22 is cylindrical in shape. The edges of the chamber 22 could, of course, be beveled or sloped to provide a wider contact area, or a beveled edge, to hold the diaphragm 18 against protruding surface 21. Thus, the diaphragm 18 may be held between a portion of the wall of the chamber 22 and the protruding surface 21. When fluid is flowing with a forward bias, the diaphragm 18 is pushed away from the protruding surface 21 and fluid flows out the holes on into chamber 22. As the elements are fitted together diaphragm 18 may be stretched or caused to be stretched.

FIG. 6 illustrates how the valve seals against backward flow. The pressure in the reverse direction of the valve causes the diaphragm 18 to seal shut against the entrance to conduit 25.

FIG. 7 illustrates the mounting of a circular diaphragm 18 between body elements 17 and 19. A flange on diaphragm 18 fits into a circular recess 26. As body element 19 is forced against body element 17, the web of diaphragm 18 is evenly and uniformly stretched over raised portion 20. By "evenly" it is meant that the diaphragm is stretched the same in one direction as another. By "uniformly" is meant that from pump to pump, all the diaphragms will have substantially the same amount of stretch, thereby causing the valves to exhibit a uniform break pressure which varied by changing the thickness of the diaphragm. The device of the invention works best when the diaphragm 18 is stretched evenly over the protrusion 20.

Figure 8:
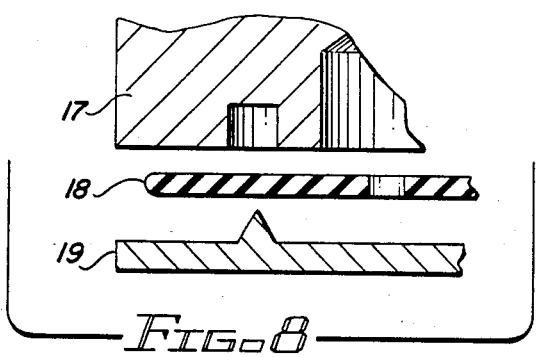
FIG. 8 illustrates another means of holding the diaphragm in place which seals against leakage.

FIG. 8 illustrates another method of tensioning and holding the diaphragm 18 in place. Body element 19 has a circular ridge which presses the diaphragm 18 into circular recess 26 of body element 17, as the valve parts are assembled. Sealing against leakage is also of concern and such structure effectively seals against leakage of the valve.

Figure 9:
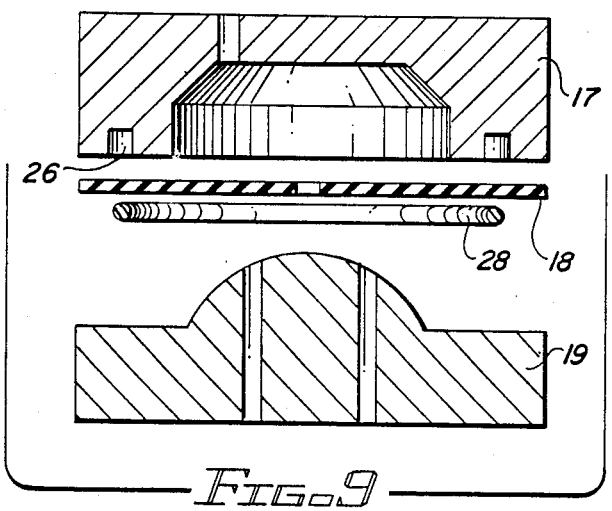
FIG. 9 shows an "O" ring used to hold the diaphragm in place and to seal against leakage.

FIG. 9 illustrates still another means for tensioning and holding the diaphragm 18 in place. "O" ring 28 (which may be a Quad ring or other sealing ring of rubber, silicone rubber, or even metal,) acts to press diaphragm 18 into recess 26 and, also, to seal the valve against leaking to the outside between the body elements 17 and 19.

Figure 10:
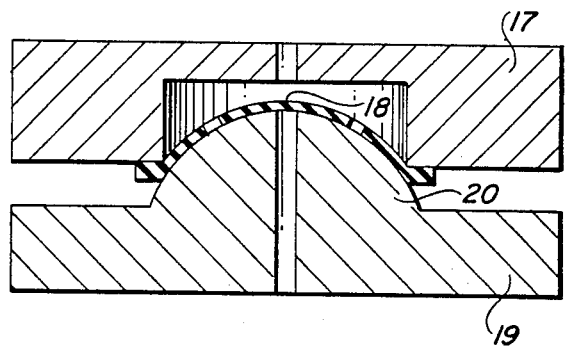
FIG. 10 illustrates another method of stretching the diaphragm between the parts of the valve.

FIG. 10 illustrates still another method of stretching elastic diaphragm 18 over protrusion 20. Diaphragm 18 in this illustration is manufactured with a flange, or lip, around its edge which is forced downwardly by the body element 17 to evenly stretch the web of the diaphragm 18 over protrusion 20.

Figure 11:
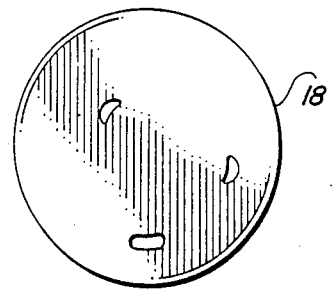
FIG. 11 illustrates a circular diaphragm having the holes therein asymmetrically located.

FIG. 11 shows diaphragm 18 with holes therethrough which are asymmetrically located and not of circular shape. It is possible that the diaphragm 18 be so constructed, depending on what is desired. The holes in the diaphragm 18 may be molded in or punched after the diaphragm 18 is manufactured.

It may be understood that the diaphragm 18 need not be constructed of uniform thickness. It may, for example, be thicker in a band in which the holes are located or at the location where it fits against the apex of the raised portion 20 or around the outside of the web. Further, the thickness of the diaphragm may vary from a central location to an outer location.

Figure 12:
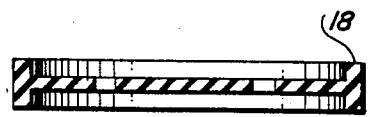
FIG. 12 shows a diaphragm having a flange portion both above and below the web of the diaphragm.

FIG. 12 illustrates a configuration of the diaphragm 18 of FIG. 7 in which a flange is also included below the diaphragm to aid in sealing the valve against leakage.

Although the invention has been described and illustrated in detail, it is to be clearly understood that the same is by way of illustration and example only and is not to be taken by way of limitation, the spirit and scope of this invention being limited only by the terms of the appended claims.

What is claimed is:

1. In combination, a valve for a medication infusion pump comprising a first body element having a protruding surface having a conduit disposed in said protruding surface through which fluid may enter said valve, a second body element having a recess having a conduit disposed therein through which fluid may leave said valve, a channel disposed in said second body element outside of said recess and around and spaced away from the circumference of said recess, said recess adapted to receive said protruding surface of said first body element therein, an elastic diaphragm located between said first and second body elements, said diaphragm having a flange which is disposed in said channel of said second body element and which is held in place by said first body element, said diaphragm being adapted to be stretched over said protruding surface of said first body element and having at least one hole disposed therethrough, said hole in said diaphragm being located within said recess and removed from said conduit in said protruding surface, and wherein said flange of said diaphragm is adapted to hold said diaphragm in place as it is placed under tension upon assembling said first body element and said second body element together.

2. A passive one-way valve for a medication infusion system, said valve comprising:
   a first body element having an essentially convex surface protruding therefrom, said convex surface having a conduit disposed therein through which fluid may enter said valve;
   a second body element having a recess disposed therein, said recess being so arranged and configured as to have an outer edge thereof forming at least a circular line of contact with said convex surface of said first body element when said first and second body elements are brought together, said second body element having a conduit disposed in said recess through which fluid may leave said valve; and
   an elastomeric diaphragm for location between said first and second body elements, said outer edge of said recess of said second body element gripping said diaphragm against said convex surface of said first body element in a sealing relationship, said diaphragm thereby being biased against said convex surface of said first body element so as to seal said conduit disposed in said convex surface, said diaphragm having at least one hole therethrough disposed away from said conduit in said convex surface when said diaphragm is located on said convex surface, said hole in said diaphragm being in fluid communication with said recess when said diaphragm is disposed between said first and second body elements, said diaphragm being forced away from said convex surface and allowing fluid flow through said valve only when fluid pressure at said conduit in said convex surface exceeds by a predetermined amount fluid pressure at said conduit in said recess.

3. A valve as defined in claim 2, wherein said diaphragm is manufactured of an elastomeric material of medical grade.

4. A valve as defined in claim 3, wherein said elastomeric material is one of the materials selected from the group consisting of silicone rubber and natural rubber.

5. A valve as defined in claim 2, wherein said first and second body elements are manufactured of one of the materials selected from the group consisting of rigid plastic and hard rubber.

6. A valve as defined in claim 5, wherein said hard plastic is one of the materials selected from the group consisting of the acrylics, polysulfins, polyethylenes, and polycarbonates.

7. A valve as defined in claim 2, wherein said conduit disposed in said convex surface of said first body element is centrally located in said convex surface and leads to the top of said convex surface.

8. A valve as defined in claim 2, wherein said diaphragm has a plurality of holes extending therethrough, which plurality of holes are disposed away from and surrounding in concentric fashion said conduit in said convex surface when said diaphragm is located on said convex surface, said plurality of holes in said diaphragm all being in fluid communication with said recess when said diaphragm is disposed between said first and second body elements.

9. A valve as defined in claim 8, wherein each of said plurality of holes is round.

10. A valve as defined in claim 2, wherein said recess is a right cylindrical recess.

11. A valve as defined in claim 2, wherein the conduit disposed in said recess of said second body element is centrally located at the location at which it emerges in said recess.

12. A valve as defined in claim 2, wherein the outer edge of said recess of said second body element is so arranged and configured as to form an annular area of contact having an area wider than said circular line of contact.

13. A valve as defined in claim 2, wherein said conduits are between 1/16 inch and $\frac{1}{8}$ inch, and said diaphragm is between 3 and 10 mils thick.

14. A valve as defined in claim 2, wherein the thickness of said diaphragm is increased to increase said predetermined amount and decreased to decrease said predetermined amount.

15. A valve as defined in claim 2, wherein the thickness of said diaphragm varies from a central location at the top of said convex surface to a location away from the center of said convex surface.

16. A valve as defined in claim 2, additionally comprising:
   a channel disposed in said second body element surrounding and spaced away from said recess; and
   a flange disposed on the side of said diaphragm facing said second body element, said flange being disposed in said channel of said second body element and being retained in said channel by said first body element.

17. A valve as defined in claim 16, additionally comprising:
   an additional flange disposed on the side of said diaphragm opposite said flange facing said second body element, said additional flange for enhancing the sealing arrangement between said first and second body elements.

18. A valve as defined in claim 16, wherein said flange is so arranged and configured as to hold said diaphragm in place for assembling said first and second body elements together, and for properly tensioning said diaphragm on said convex surface.

19. A passive one-way valve for use with the pump of a infusion system, comprising:
   a first body element having a convex surface protruding therefrom, said convex surface having a conduit centrally disposed therein through which fluid may enter said valve;
   a second body element having a right cylindrical recess disposed therein, an outer edge of said recess forming a circular line of contact with said convex surface of said first body element when said first and second body elements are brought together, said second body element having a conduit disposed in said recess through which fluid may leave said valve, said second body element having a channel disposed therein surrounding and spaced away from said recess; and an essentially flat elastomeric diaphragm for location between said first and second body elements, said diaphragm having a flange which is disposed in said channel of said second body element and which is retained in said channel by said first body element, said diaphragm thereby being biased against said convex surface of said first body element so as to seal said conduit disposed in said convex surface, said diaphragm having a plurality of holes therethrough disposed away from and surrounding in concentric fashion said conduit in said convex surface when said diaphragm is located on said convex surface, said plurality of holes in said diaphragm being in fluid communication with said recess when said diaphragm is disposed between said first and second body elements, said diaphragm being forced away from said convex surface and allowing fluid flow through said valve only when fluid pressure at said conduit in said convex surface exceeds by a predetermined amount fluid pressure at said conduit in said recess.

20. A valve assembly for a medication infusion system, said valve assembly comprising:

a first body element;

a second body element;

a first essentially convex surface protruding from said first body element, said first convex surface having a conduit disposed therein through which fluid may enter;

a second essentially convex surface protruding from said second body element, said second convex surface having a conduit disposed therein through which fluid may enter;

a first recess disposed in said second body element, said first recess being so arranged and configured as to have an outer edge thereof forming at least a circular line of contact with said first convex surface of said first body element when said first and second body elements are brought together, said second body element having a conduit disposed in said first recess through which fluid may leave;

a second recess disposed in said first body element, said second recess being so arranged and configured as to have an outer edge thereof forming at least a circular line of contact with said second convex surface of said second body element when said first and second body elements are brought together, said first body element having a conduit disposed in said second recess through which fluid may leave;

a first elastomeric diaphragm for location between said first and second body elements, said outer edge of said first recess of said second body element gripping said first diaphragm against said first convex surface of said first body element in a sealing relationship, said first diaphragm thereby being biased against said first convex surface of said first body element so as to seal said conduit disposed in said first convex surface, said first diaphragm having at least one hole therethrough disposed away from said conduit in said first convex surface when said first diaphragm is located on said first convex surface, said hole in said first diaphragm being in fluid communication with said first recess when said first diaphragm is disposed between said first and second body elements, said first diaphragm being forced away from said first convex surface and allowing fluid flow only when fluid pressure at said conduit in said first convex surface exceeds by a first predetermined amount fluid pressure at said conduit in said first recess; and a second elastomeric diaphragm for location between said first and second body elements, said outer edge of said second recess of said first body element gripping said second diaphragm against said second convex surface of said second body element in a sealing relationship, said second diaphragm thereby being biased against said second convex surface of said second body element so as to seal said conduit disposed in said second convex surface, said second diaphragm having at least one hole therethrough disposed away from said conduit in said second convex surface when said second diaphragm is located on said second convex surface, said hole in said second diaphragm being in fluid communication with said second recess when said second diaphragm is disposed between said first and second body elements, said second diaphragm being forced away from said second convex surface and allowing fluid flow only when fluid pressure at said conduit in said second convex surface exceeds by a second predetermined amount fluid pressure at said conduit in said second recess.

21. A valve assembly as defined in claim 20, wherein said first and second diaphragms are manufactured of a single flat segment of elastomeric material.

* * * * *